(12) United States Patent
Nakamura

(10) Patent No.: US 9,987,091 B2
(45) Date of Patent: Jun. 5, 2018

(54) MEDICAL INSTRUMENT

(71) Applicant: Shoichi Nakamura, Nagano (JP)

(72) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 181 days.

(21) Appl. No.: 14/241,718

(22) PCT Filed: Feb. 27, 2013

(86) PCT No.: PCT/JP2013/055157
§ 371 (c)(1),
(2) Date: Feb. 27, 2014

(87) PCT Pub. No.: WO2013/179707
PCT Pub. Date: Dec. 5, 2013

(65) Prior Publication Data
US 2014/0343588 A1    Nov. 20, 2014

(30) Foreign Application Priority Data

May 30, 2012    (JP) .................................. 2012-122777

(51) Int. Cl.
*A61B 17/32*    (2006.01)
*A61B 19/00*    (2006.01)
(Continued)

(52) U.S. Cl.
CPC .......... *A61B 19/22* (2013.01); *A61B 17/0218* (2013.01); *A61B 17/3211* (2013.01);
(Continued)

(58) Field of Classification Search
CPC . A61B 1/0051; A61B 1/0058; A61B 17/3211; A61B 17/3213;
(Continued)

(56) References Cited

U.S. PATENT DOCUMENTS 2,525,181 A * 10/1950 Ransdell ................ A61B 1/247
433/30
5,254,130 A * 10/1993 Poncet .................... A61B 17/29
600/564

(Continued)

FOREIGN PATENT DOCUMENTS

JP    2004141593    *    4/2004
JP    2004141593    *    5/2004

(Continued)

OTHER PUBLICATIONS

Translation JP3498092 Accessed Sep. 19, 2015 from https://www.j-platpat.inpit.go.jp/web/all/top/BTmTopEnglishPage.*
(Continued)

*Primary Examiner* — Katrina Stransky
*Assistant Examiner* — Kankindi Rwego
(74) *Attorney, Agent, or Firm* — Manabu Kanesaka

(57) ABSTRACT

A medical instrument includes a rod-shaped grasp portion at a base end thereof, a functional portion used in medical practice at a front end thereof, and a shape-memory portion including a rod-shaped shape-memory alloy provided between the grasp portion and the functional portion. The grasp portion includes a holding portion having a space in which one end of the shape-memory portion is inserted from the longitudinal direction. The instrument has a gap between an outer surface of the shape-memory portion and an inner surface of the holding portion, and in bending the shape-memory portion, the shape-memory portion is capable of deforming within the range of the gap. Then, by bending, the outer surface of the shape-memory portion comes into contact with an inner edge portion of an opening of the holding portion, and thereby restricts deformation of the shape-memory portion beyond the predetermined range.

8 Claims, 11 Drawing Sheets

(51) Int. Cl.
*A61B 17/02* (2006.01)
*A61B 17/3213* (2006.01)
*A61B 17/3211* (2006.01)
*A61M 29/00* (2006.01)
*G02B 7/182* (2006.01)
*A61B 34/00* (2016.01)
*A61B 1/247* (2006.01)
*A61B 17/00* (2006.01)
*A61B 17/22* (2006.01)
*A61B 1/00* (2006.01)

(52) U.S. Cl.
CPC .......... *A61B 17/3213* (2013.01); *A61B 34/70* (2016.02); *A61M 29/00* (2013.01); *G02B 7/182* (2013.01); *A61B 1/0011* (2013.01); *A61B 1/247* (2013.01); *A61B 2017/00331* (2013.01); *A61B 2017/00867* (2013.01); *A61B 2017/22001* (2013.01); *A61B 2017/320044* (2013.01)

(58) Field of Classification Search
CPC ........... A61B 2017/00867; A61B 2017/00331; A61B 2017/00336; A61B 17/22031; A61B 17/22032; A61B 2017/22034; A61B 2017/22035; A61B 1/24; A61B 1/247; A61B 1/253; A61B 1/267; A61B 1/2673; A61B 1/2676; A61B 1/273; A61B 1/2733; A61B 1/2736; A61B 1/303; A61B 1/307; A61B 1/31; A61B 1/313; A61B 1/3132; A61B 1/3135; A61B 1/3137; A61B 1/32; A61B 17/285; A61B 17/295; A61C 3/00; A61C 3/005; A61C 3/02; A61C 3/025; A61C 3/03; A61C 3/04; A61C 3/06; A61C 3/08; A61C 3/10; A61C 3/12; A61C 3/14; A61C 3/16; A61C 3/162; A61C 3/164; A61C 3/166; A61C 3/168; A61M 2025/0175; A61M 2005/31598; A61M 5/3297
USPC ..... 606/167; 30/329, 330, 340, 343; 81/487, 81/489, 491; 604/93.01, 164.1, 164.11, 604/164.12, 164.13, 165.01, 165.02, 604/165.03, 165.04, 166.01, 167.01, 604/167.02, 167.03, 167.04, 167.05, 604/167.06, 168.01, 170.01, 170.02, 604/170.03, 171
See application file for complete search history.

(56) References Cited

U.S. PATENT DOCUMENTS

| | | | | |
|---|---|---|---|---|
| 5,607,435 | A | * | 3/1997 | Sachdeva ............. A61B 1/0058 359/819 |
| 5,749,879 | A | * | 5/1998 | Middleman ........... A61B 10/02 606/139 |
| 6,702,577 | B2 | * | 3/2004 | Wong ................... A61B 1/0669 433/30 |
| 7,021,780 | B2 | * | 4/2006 | Kasem .................. G02B 7/182 359/881 |
| 8,100,837 | B1 | * | 1/2012 | Cornish ................ A61M 25/09 600/585 |
| 2008/0015625 | A1 | * | 1/2008 | Ventura .............. A61B 17/3439 606/191 |
| 2008/0275483 | A1 | * | 11/2008 | Makower ................ A61B 17/24 606/192 |
| 2009/0281617 | A1 | * | 11/2009 | Cottone .................. A61F 2/958 623/1.23 |
| 2010/0030113 | A1 | * | 2/2010 | Morriss .................. A61B 1/233 600/585 |

FOREIGN PATENT DOCUMENTS

| | | |
|---|---|---|
| JP | 2007-037777 A | 2/2007 |
| JP | 3980989 B2 | 7/2007 |
| WO | WO2011129508 A1 * | 10/2011 |

OTHER PUBLICATIONS

Translation KR2010008030 WO 2011129508 Accessed Apr. 18, 2016 from https://patentscope/wipo.int/search/en/.*
PCT/ISA/237, "Written Opinion of the International Searching Authority for PCT/JP2013/055157", dated May 21, 2013.
PCT/ISA/210, "International Search Report for PCT/JP2013/055157", dated May 21, 2013.

* cited by examiner

FIG. 10A
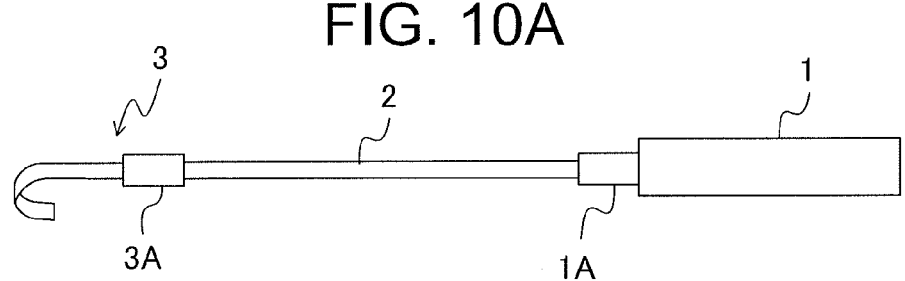
FIG. 10B
(i) 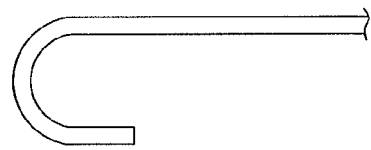   (ii) 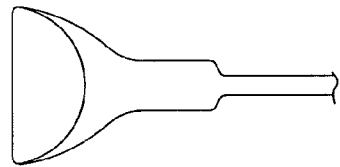
FIG. 10C
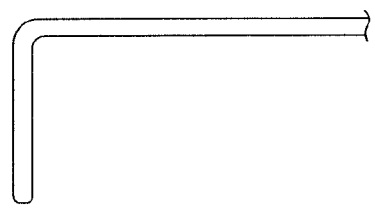   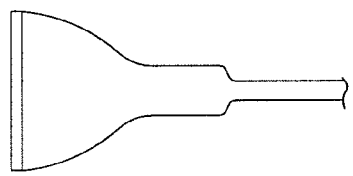

FIG. 11A
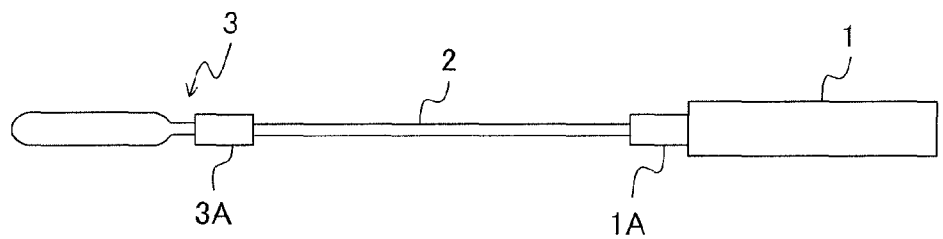
FIG. 11B  FIG. 11C  FIG. 11D
 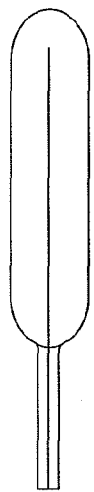 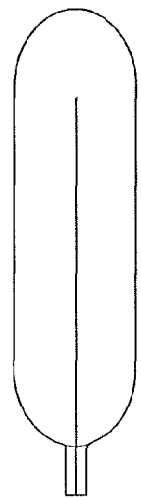

MEDICAL INSTRUMENT

RELATED APPLICATIONS

The present application is National Phase of International Application No. PCT/JP2013/055157 filed Feb. 27, 2013, and claims priority from Japanese Application No. 2012-122777, filed May 30, 2012.

TECHNICAL FIELD

The present invention relates to medical instruments such as a knife, mirror, hook, retractor and dilator used in the medical field, and more particularly, to medical instruments that enable a functional portion provided at the front end of the instrument to be displaced at a required angle when the instrument is used in a medical operation.

BACKGROUND ART

In medical instruments each provided with a rod-shaped grasp portion at its base end and a functional portion such as a knife, mirror, hook, retractor and dilator used in medical practice at its front end, it has conventionally been general that the grasp portion and the functional portion are arranged substantially linearly.

FIGS. 12 to 14 show one example of such conventional medical instruments. FIG. 12 is a schematic view showing an example of the conventional medical knife, and FIG. 13 is a schematic view showing an example of the conventional medical mirror.

A medical knife 101 shown in FIG. 12 has a rod-shaped grasp portion 102 at its base end, while being provided with a knife body 104 as a functional portion at its front end. Further, a medical mirror 201 as shown in FIG. 13 has a rod-shaped grasp portion 202 at its base end, while being provided with a mirror body 204 as a functional portion at its front end. As shown in the figures, the grasp portions 102 and 202 and the functional portions 104 and 204 are arranged substantially in the straight line fixedly, respectively.

However, for example, in heart coronary-artery bypass surgery and the like, from the relationship between the position of a blood vessel to cut and an insertion angle of the medical knife, the conventional medical knife as shown in FIG. 12 sometimes hides the knife front end in the hand of the operator, and therefore, in such a medical knife 101 in which the grasp portion 102 and knife body 104 are arranged in the straight line as described above, there is a problem that the knife 101 is hard to see and use in cutting.

Then, such medical knives have previously been commercially available that a removable knife body can be disposed at an arbitrary angle with respect to the grasp portion (for example, Patent Document 1). FIG. 14 shows a conventional medical knife. The medical knife 301 is comprised of a grasp portion 302, and a knife body (functional portion) 304 in the shape of a "C". Since the knife body 304 is bent in the shape of a "C", while a connection portion between the grasp portion 302 and the knife body 304 is bent, it is possible to attach the blade at a certain angle with respect to the grasp portion 302. Prepared as the knife body 304 is a plurality of kinds with different bending angles, and as necessary, the knife body 304 with an arbitrary angle is attached and used.

Meanwhile, the medical mirror 201 is used to visually identify an area such as a deep narrow operation site and the inside of the oral cavity that are normally hard to see, and conventionally, as shown in FIG. 13, by attaching the mirror body 204 at an angle with respect to the grasp portion 202, an observation object is made easy to see.

In the case of the above-mentioned conventional medical knife 301 as shown in FIG. 14, since the bending angle of the knife body 304 is beforehand set, there is a problem that the angle of the knife body 304 can only be changed stepwise. In other words, versatility of the change angle of the knife body 304 is low, and it is not possible to set a delicate angle corresponding to the situation. Further, in the case of desiring to change to a different angle during the treatment, there is a problem of preparing the new medical knife 301 again, or of removing the knife body 304 from the grasp portion 302 to replace with the knife body 304 with a different bending angle.

Therefore, medical instruments deformable to a bent state and changeable in the position have been known using shape-memory alloys in a part of some middle portion of a shaft portion formed between the functional portion and the grasp portion (for example, Patent Document 2).

PRIOR ART DOCUMENT

Patent Document

Patent Document 1: Japanese Patent Gazette No. 3980989
Patent Document 2: Japanese Patent Application Publication No. 2007-37777

DISCLOSURE OF INVENTION

Problems to be Solved by the Invention

However, the shape-memory alloy is to return to its original shape with respect to a bend (distortion) within 10% of the metal crystalline structure when a predetermined temperature is applied, and is not able to return to its original shape when extreme deformation such that the metal crystalline structure changes is applied. Therefore, the shape-memory alloy can be bent only in the range of small angles, and there is a case that it is not possible to secure a necessary bending angle when used in a medical operation.

By increasing the dimension in the longitudinal direction of the shape-memory portion using the shape-memory alloy, it is possible to deform largely in bending with the same curvature radius, but when the shape-memory portion is simply made long, corresponding thereto, the dimensions of the instrument are longer to be hard to handle, and there is a problem that operability deteriorates.

Therefore, in view of the above-mentioned respects, it is an object of the present invention to provide a medical instrument that enables a functional portion to be displaced adequately even when the bending angle is small, by making a structure that enables a large dimension in the longitudinal direction of the shape-memory portion to be secured without particularly increasing the length dimension of the entire instrument in the medical instrument using the shape-memory alloy.

Means for Solving the Problem

To attain the above-mentioned object, the present invention provides a medical instrument characterized by having a rod-shaped grasp portion at a base end thereof, a functional portion used in medical practice at a front end thereof, a shape-memory portion comprised of a rod-shaped shape-memory alloy provided between the grasp portion and the functional portion, and a holding portion, formed in the grasp portion, having a space in which apart of the shape-memory portion is inserted from a longitudinal direction, where a gap is provided between an inner surface of the holding portion and an outer surface of the shape-memory portion, the shape-memory portion is subjected to memory treatment in a linear state, is bent within a predetermined range as necessary to use, and after using, is returned to an original memory-treated shape by heating the shape-memory portion to a memory recovery temperature, and in bending the shape-memory portion, the outer surface of the shape-memory portion comes into contact with an inner edge portion at a front end of an opening of the holding portion, and thereby restricts deformation of the shape-memory portion beyond the predetermined range. At this point, it is preferable to provide surfaces of the grasp portion and the functional portion with knurling processing and/or satin finish in order for fingers not to slip when an operator grasps to operate.

Further, the shape-memory portion is characterized by being comprised of a nickel-titanium alloy. Then, the functional portion is characterized by being any one of a medical knife, medical mirror, medical hook, medical retractor and dilator.

Furthermore, it is a feature that the opening of the holding portion is extended and opened toward the functional portion.

Still furthermore, the functional portion is characterized by further having a receiving portion, in which a front end portion of the shape-memory portion is inserted, at a connection portion with the shape-memory portion, where a gap is provided between an inner surface of the receiving portion and an outer surface of the shape-memory portion, and in bending the shape-memory portion, the outer surface of the shape-memory portion comes into contact with an inner edge portion at a front end of an opening of the receiving portion, and thereby restricts deformation of the shape-memory portion beyond the predetermined range. Then, it is a feature that the opening of the receiving portion is extended and opened in the direction of the grasp portion.

The medical mirror is characterized by being configured by coupling a pair of mirrors in the shape of a hinge, where the shape-memory portion is connected to the shaft of the hinge. Further, another one of the medical mirror is characterized by being formed in the shape of a cone with the connection portion with the shape-memory portion being the vertex, where an inner surface of the cone is a mirror surface.

To attain the above-mentioned object, the present invention provides a medical instrument characterized by having a rod-shaped grasp portion at a base end thereof, a functional portion used in medical practice at a front end thereof, a shape-memory portion comprised of a rod-shaped shape-memory alloy provided between the grasp portion and the functional portion, and a holding portion formed in the grasp portion to cover an entire outer surface of a part of the shape-memory portion on the base end side with a flexible material, where the shape-memory portion is subjected to memory treatment in a linear state, is bent within a predetermined range as necessary to use, and after using, is returned to an original memory-treated shape by heating the shape-memory portion to a memory recovery temperature, and in bending the shape-memory portion, an elastic force of the holding portion restricts deformation of the shape-memory portion beyond the predetermined range.

Then, it is a feature that a thickness of a cover portion to cover the shape-memory portion in the holding portion is formed to be thinner toward the functional portion.

Advantageous Effect of the Invention

According to the medical instrument of the invention, it is possible to secure largely the dimension in the longitudinal direction by inserting a part of the shape-memory portion in the inside of the holding portion, and it is possible to largely displace the functional portion even in a small bending angle of the shape-memory portion.

Further, in bending the shape-memory portion, the shape-memory portion is restricted to the deformation limit when the outer surface of the shape-memory portion comes into contact with the inner edge portion at the front end of the opening of the holding portion, and it is thereby possible to prevent the shape-memory portion from being bent beyond the predetermined rage.

BRIEF DESCRIPTION OF DRAWINGS

FIG. 10A is an entire front view showing a medical instrument (medical retractor) according to the Embodiment of the invention; FIGS. 10B and 10C are explanatory views showing typical examples of the retractor body shape;

FIG. 11A is an entire front view showing a medical instrument (dilator) according to the Embodiment of the invention; FIGS. 11B to 11D are explanatory views showing typical examples of the dilator body shape;

BEST MODE FOR CARRYING OUT THE INVENTION

An Embodiment of the present invention will specifically be described below with reference to drawings.

Figure 1:
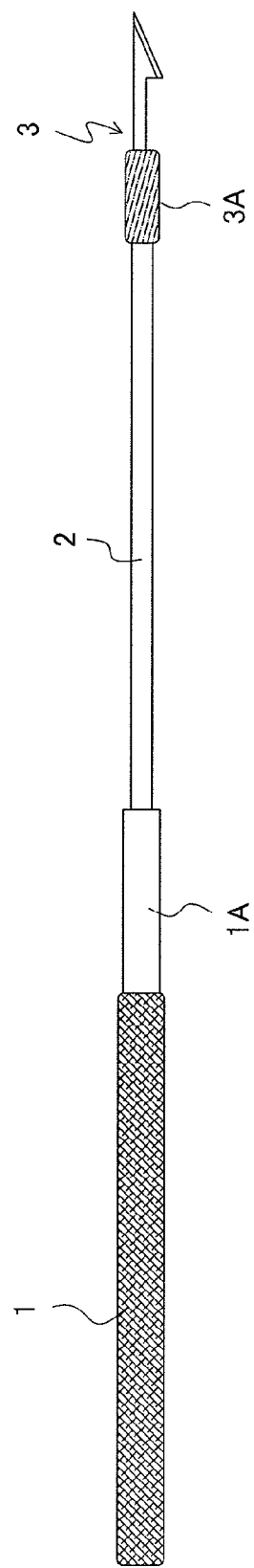
FIG. 1 is an entire front view showing a medical instrument (medical knife) according to an Embodiment of the invention.

FIG. 1 is an entire front view showing the outline of a medical instrument according to the invention. As shown in FIG. 1, the medical instrument (herein, medical knife) of this Embodiment is comprised of a rod-shape grasp portion 1, a shape-memory portion 2 connected to the front end of the grasp portion 1, a functional portion 3 disposed at the front end of the shape-memory portion 2, a holding portion 1A, formed in the grasp portion 1, having a space in which is inserted one end of the shape-memory portion 2, and a receiving portion 3A, formed in the functional portion 3, having a space in which is inserted the other end of the shape-memory portion 2.

The grasp portion 1 is a portion for a user to grasp in using, and is a rod-shaped member made of metal such as a titanium alloy and stainless steel. Knurling processing and/or satin finish is provided around the grasp portion 1 in order for fingers not to slip when the user grasps to operate.

The shape-memory portion 2 is a rod-shaped member made of a shape-memory alloy such as Nitinol (nickel-titanium alloy). The shape-memory alloy is a specific alloy which remembers some shape by heat treatment, and when deformed, returns to the pre-deformed shape by heating to a predetermined temperature or more. As shown in FIG. 1, the shape-memory portion 2 is subjected to memory treatment in a straight linear state. Then, the shape-memory portion 2 is deformed by a force of the degree of applying by an adult using both hands and/or a device (a pair of pliers, or the like), and is provided with flexibility/rigidity of the degree of not deforming during the use in surgery and the like.

Figure 6:
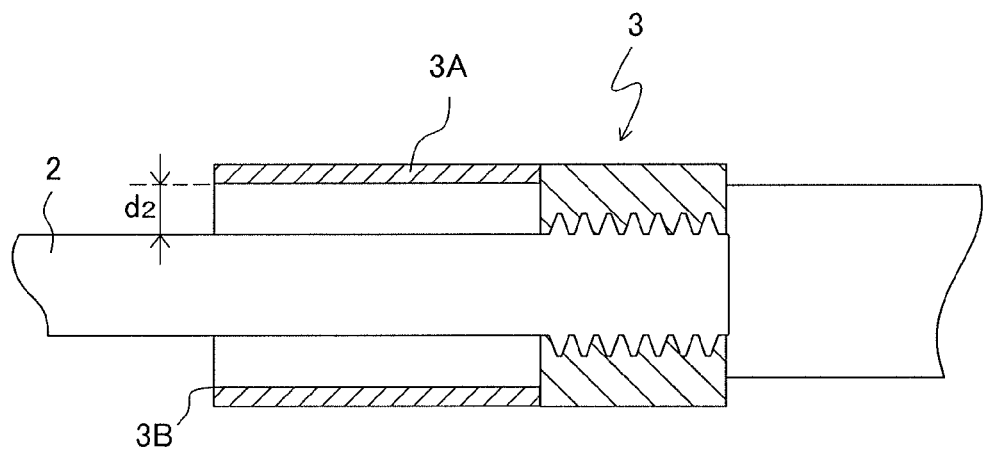
FIG. 6 is an explanatory view showing the relationship between a receiving portion and the shape-memory portion in the medical instrument as shown in FIG. 1.

The functional portion 3 is herein a knife body, and is disposed at the front end of the shape-memory portion 2. Then, the functional portion 3 is provided with a receiving portion 3A, in which the shape-memory portion 2 is inserted, on the connection side to the shape-memory portion 2, and as shown in FIG. 6, the shape-memory portion 2 inserted from the receiving portion 3A is connected to the functional portion 3 by fastening a screw. As kinds of the functional portion 3, as well as the knife body, there are a mirror body, hook body and the like used in the medical field, and any bodies have the receiving portion 3A in which the shape-memory portion 2 is inserted. As in the grasp portion 1, knurling processing and/or satin finish is provided around the surface of the receiving portion 3A in order for fingers not to slip when an operator grasps to operate.

The holding portion 1A has the shape of a pipe, and is integrally formed as apart of the grasp portion 1. Then, apart of the shape-memory portion 2 on the base end side is inserted in the inside of the holding portion 1A, and as in connection with the functional portion 3 as shown in FIG. 6, the portion 2 is connected to the grasp portion 1 by fastening a screw.

The grasp portion 1, shape-memory portion 2 and functional portion 3 are connected mutually detachably, and as the connection method, as well as the screw scheme as described above, it is possible to apply various schemes such as a fit scheme. Further, the receiving portion 3A may be configured as a different form from the functional portion 3 to be detachable by a screw scheme, fit scheme or the like. Furthermore, the holding portion 1A may also be configured as a different form from the grasp portion 1 to be detachable by a screw scheme, fit scheme or the like.

Figure 3:
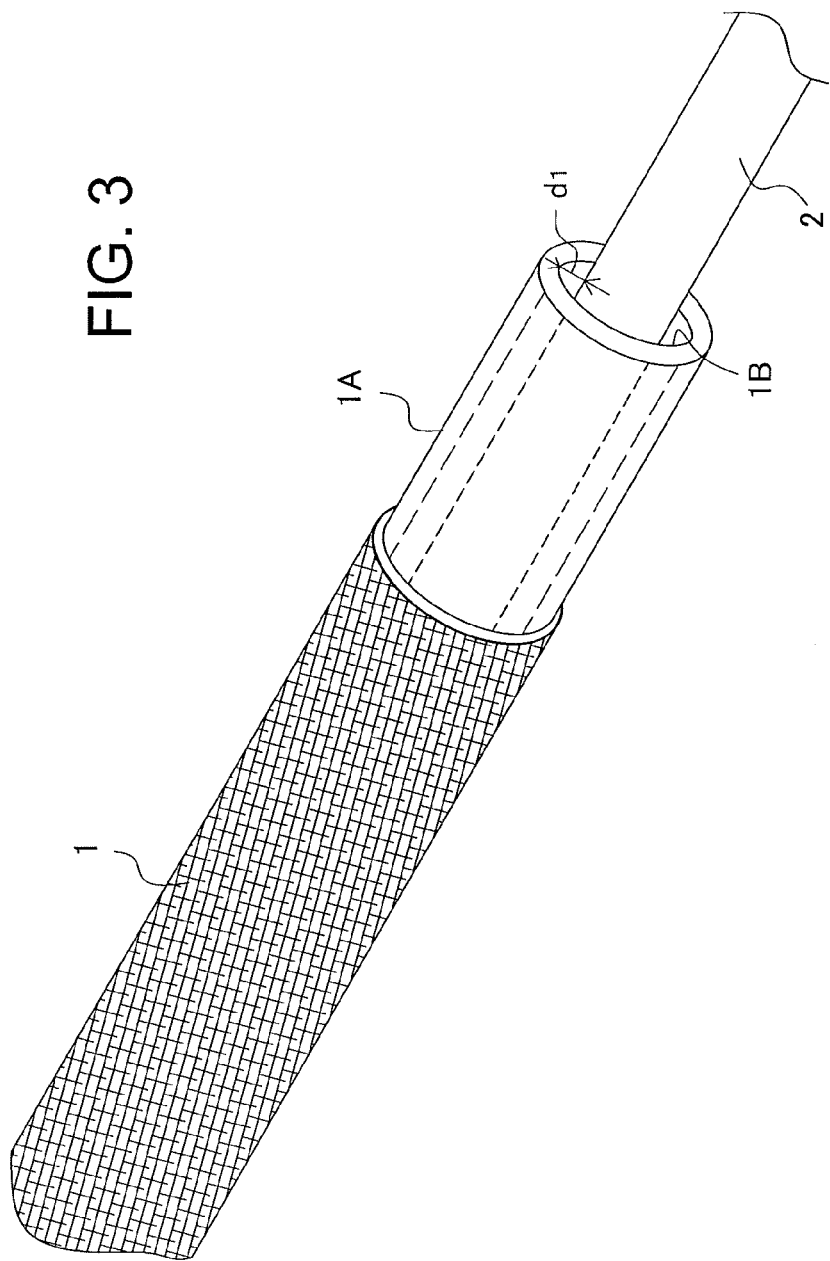
FIG. 3 is an explanatory view showing the relationship between a holding portion and the shape-memory portion in the medical instrument as shown in FIG. 1.

Thus, both ends of the shape-memory portion 2 are respectively inserted in hollow portions of the holding portion 1A and receiving portion 3A, and gaps $d_1$, (FIG. 3) and $d_2$ (FIG. 6) are respectively provided so that the outer surface of the shape-memory portion 2 does not contact the inner surfaces of the holding portion 1A and receiving portion 3A when the shape-memory portion 2 is in a straight linear state. The gaps $d_1$ and $d_2$ exist, and therefore, in bending, the shape-memory portion 2 is able to deform freely also in the portions inserted in the holding portion 1A and receiving portion 3A. Accordingly, the holding portion 1A is formed in a part of the grasp portion 1, the receiving portion 3A is formed in a part of the functional portion 3, both ends of the shape-memory portion 2 are respectively inserted therein, a large dimension is thereby secured in the shape-memory portion 2 corresponding to the dimensions in the longitudinal direction of the holding portion 1A and the receiving portion 3A, and it is possible to make the dimension of the shape-memory portion 2 long. In addition, dimensions of the gap $d_1$ and $d_2$ will be clarified later.

Thus, by largely securing the dimension length in the longitudinal direction of the shape-memory portion 2, when the dimension is long in bending, as compared with the case of being short, the shift amounts of both ends of the shape-memory portion 2 are larger in the case of being long in bending with the same curvature radius. Accordingly, with respect to the grasp portion 1 side of the shape-memory portion 2 as a reference, the functional portion 3 is relatively displaced larger as the dimension in the longitudinal direction of the shape-memory portion 2 is longer. Therefore, as the shape-memory portion 2 is longer, versatility is higher in displacement of the functional portion 3 by adjustments of the bending angle, and it is possible to adjust a bend of the functional portion 3 from the grasp portion 1 to an optimal angle easy to conduct an operation.

Further, while the length dimension of the shape-memory portion 2 is secured by providing the holding portion 1A and the receiving portion 3A, it is further effective increasing the substantial dimension of the shape-memory portion 2 within the scope of not resulting in deterioration of operability.

On the other hand, when the shape-memory portion 2 becomes long, since it is made possible to bend from both ends by a small force, there is the risk that the portion may be bent more than the deformation limit angle, and that it is not possible to return to the original linear state.

Thus, in bending more than the deformation limit angle beyond the predetermined range, the outer surface of the shape-memory portion 2 comes into contact with an inner edge portion 1B at the front end of the opening of the holding portion 1A, and then, comes into contact with an inner edge portion 3B at the front end of the opening of the receiving portion 3A, and it is restricted bending more than the deformation limit angle. Further, since the shape-memory portion 2 is supported by the holding portion 1A, it is possible to transfer the force from the grasp portion 1 or holding portion 1A to the functional portion 3 reliably in operating the instrument.

Accordingly, dimensions of the gap $d_1$ are set so that the bend, such that the outer surface of the shape-memory portion 2 comes into contact with the inner edge portion at the front end of the opening of the holding portion 1, remains within the predetermined range of the deformation limit angle or less of the shape-memory portion 2, in grasping the grasp portion 1 and the receiving portion 3A and bending the shape-memory portion 2 from both ends. Similarly, at the other end of the shape-memory portion 2, dimensions of the gap $d_2$ are set so that the bend, such that the outer surface of the shape-memory portion 2 comes into contact with the inner edge portion at the front end of the opening of the receiving portion 3A, is the deformation limit angle of the shape-memory portion 2.

Figure 4:
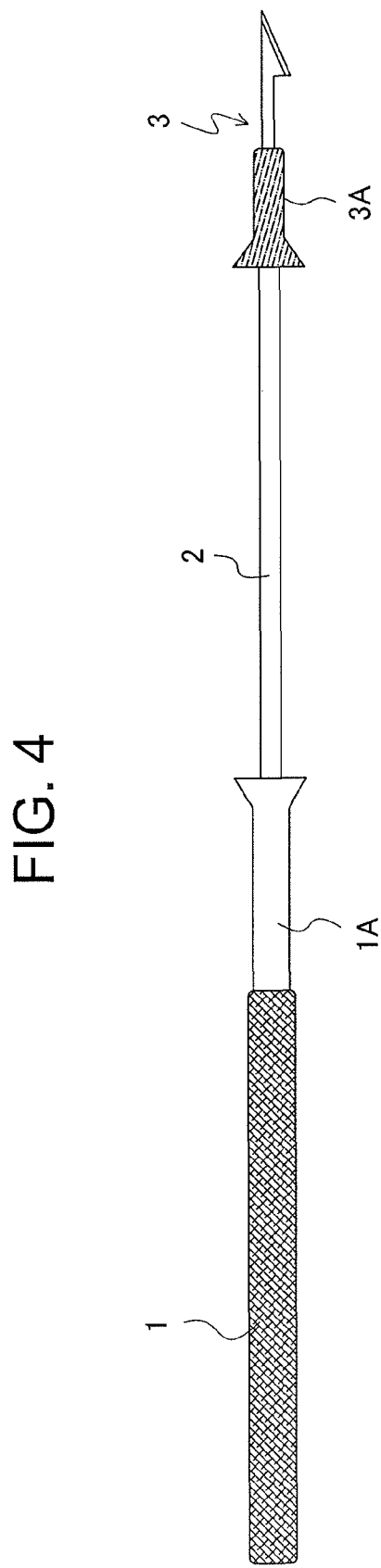
FIG. 4 is an entire front view showing another example of the medical instrument (medical knife) according to the Embodiment of the invention.
Figure 5:
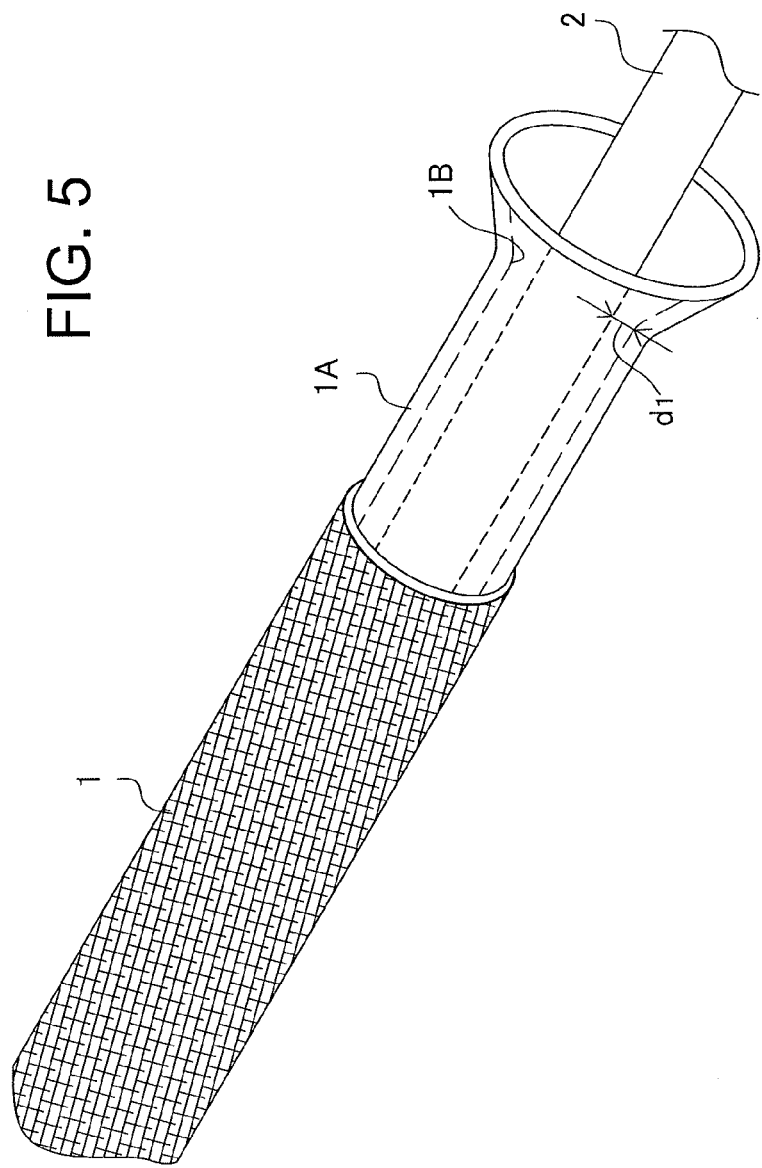
FIG. 5 is an explanatory view showing the relationship between a holding portion and a shape-memory portion in the medical instrument as shown in FIG. 4.

Further, as shown in FIG. 4, by making the shape such that each opening portion is extended and opened toward the front end, the range of bending of the shape-memory portion 2 increases, and by this means, it is possible to prevent the occurrence of a situation in which the portion 2 is bent at an acute angle with respect to contact points, as a fulcrum, with the inner edge portion 1B at the front end of the opening of the holding portion 1A and the inner edge portion 3B at the front end of the opening of the receiving portion 3A, and is not able to return to the linear state later. FIG. 5 shows the specific case of the holding portion 1A. The opening portion is extended and opened to be larger than the dimension of the gap $d_1$ from the inner edge portion 1B of the opening on the functional portion 3 side in the holding portion 1A, as a starting point. Although not shown, the receiving portion 3A is in the same manner, and the front end of the opening portion on the holding portion 1A side of the receiving portion 3A is extended and opened to be larger than the gap $d_2$.

In this Embodiment, by the holding portion 1A and receiving portion 3A, it is restricted that bending of the shape-memory portion 2 is more than the deformation limit angle, and the restriction may be made only by the holding portion 1A. However, by adding restrictions from both ends of the shape-memory portion 2, it is intended to reliably prevent bending from being more than the deformation limit angle. Moreover, since both ends of the shape-memory portion 2 are supported by the holding portion 1 and the receiving portion 3A in bending, the force in bending is distributed over the whole of the shape-memory portion 2, and it is possible to prevent the shape-memory portion 2 from bending at an acute angle by the bending force concentrating on one point of the shape-memory portion 2.

Figure 7:
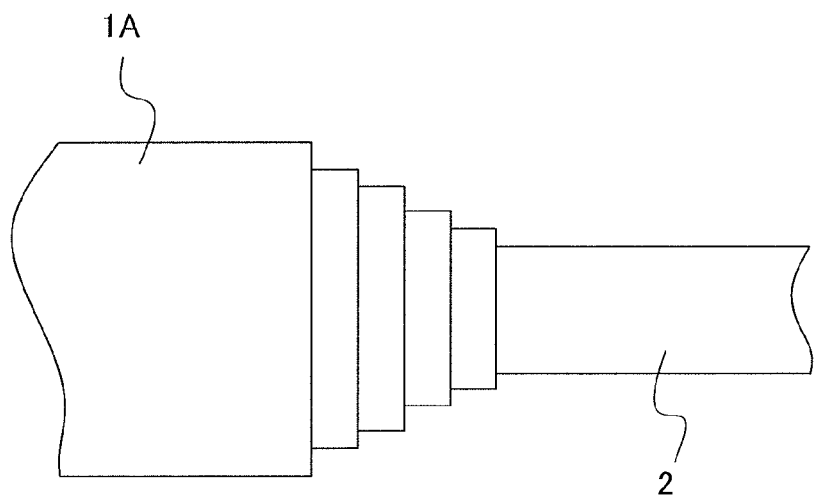
FIG. 7 is an explanatory view showing a modification of the holding portion.

FIG. 7 shows a modification of the holding portion 1A in the medical instrument of FIG. 1. The holding portion 1A in FIG. 7 is also a part of the grasp portion 1, is made of a flexible material, and covers the entire outer surface of a part of the shape-memory portion 2 on the base end side. Accordingly, since the holding portion 1A deforms together with the shape-memory portion 2 in bending, as the shape-memory portion 2, the large length dimension is secured including the cover portion. Meanwhile, by the elastic force of the flexible material, it is restricted that the shape-memory portion 2 deforms beyond the predetermined range.

At this point, the thickness of the cover portion to cover the shape-memory portion 2 is configured to be thinner toward the functional portion 3 so as to gradually decrease the elastic force exerted on the shape-memory portion 2, and the shape-memory portion 2 is thereby prevented from bending sharply in the boundary portion with the holding portion 1. In this Example, the thickness of the cover portion is made thinner stepwise, and may also be formed in the shape of a taper.

Figure 2:
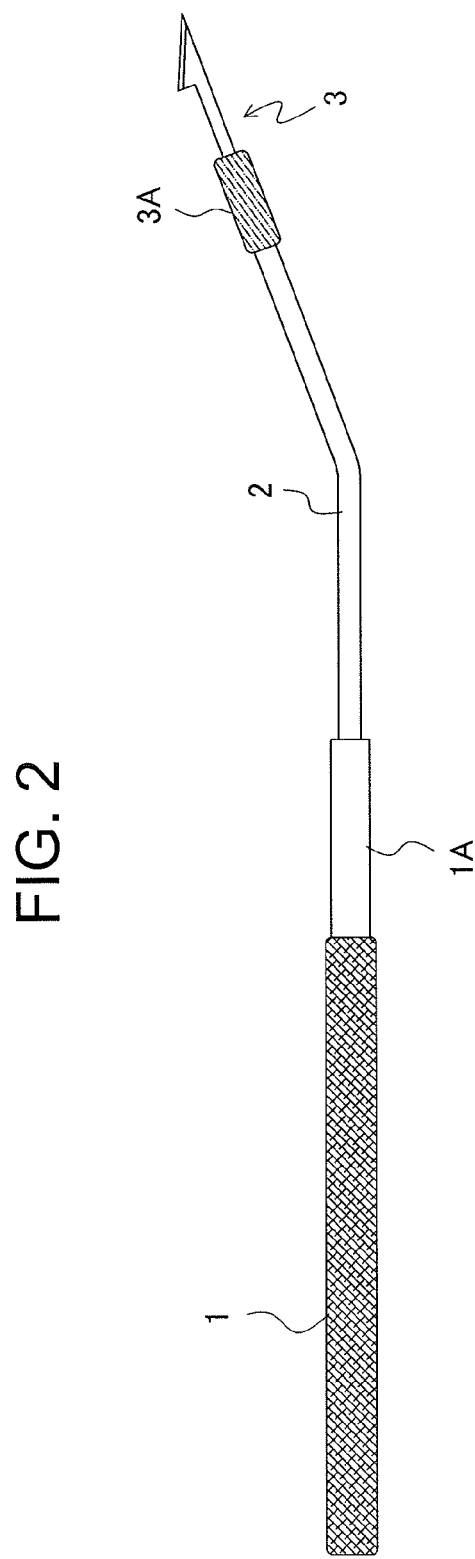
FIG. 2 is an entire front view showing a state of bending a shape-memory portion of the medical instrument as shown in FIG. 1.

In using the medical knife of above-mentioned this Embodiment, as shown in FIG. 2, an operator applies the force to the shape-memory portion 2 to bend, when necessary, using a pair of pliers or dedicated assistive device (not shown), or manually. Herein, in order to easily bend the shape-memory portion 2 corresponding to each shape of the medical knife, medical mirror, medical hook, medical retractor or dilator by a small force, for example, preferable as the dedicated assistive device are devices using the principles of leverage. Further, the dedicated assistive device may be provided with a heating means (electric heating) to heat the shape-memory portion 2 of the medical instrument. By this means, it is possible to provide the functional portion 3 with an optional angle with respect to the grasp portion 1.

After using, the functional portion 3 is removed, and the shape-memory portion 2 is heated to the memory recovery temperature, and then, returns to the original shape i.e. straight shape as shown in FIG. 1. For example, it is suitable that the memory recovery temperature of the shape-memory portion 2 is set at about 100° C., and in this case, it is possible to recover the shape with ease by boiling or exposing to steam for sterilization.

In addition, in the above-mentioned description, as the medical knife, the blade protruding substantially in the shape of a triangle is illustrated as an example, and as well as the shape, it is possible to attach various shapes of blades.

Further, in the above-mentioned description, the medical knife is described as the medical instrument, and as well as the knife, it is possible to apply various members to the functional portion 3. As described above, in the medical instrument according to the invention, the functional portion 3 is adjusted optimally to a position facing the observation site, and therefore, by making a mirror body used in the functional portion 3 a particular shape, it is possible to perform further effective observation.

Figure 8A:
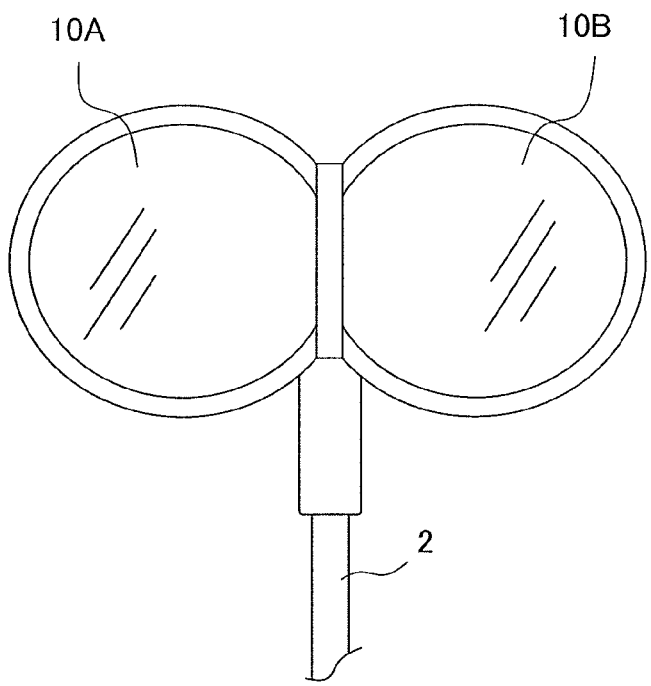
FIGS. 8A and 8B contain explanatory views showing an example of a mirror when a functional portion is a medical mirror in the medical instrument according to the Embodiment of the invention.
Figure 8B:
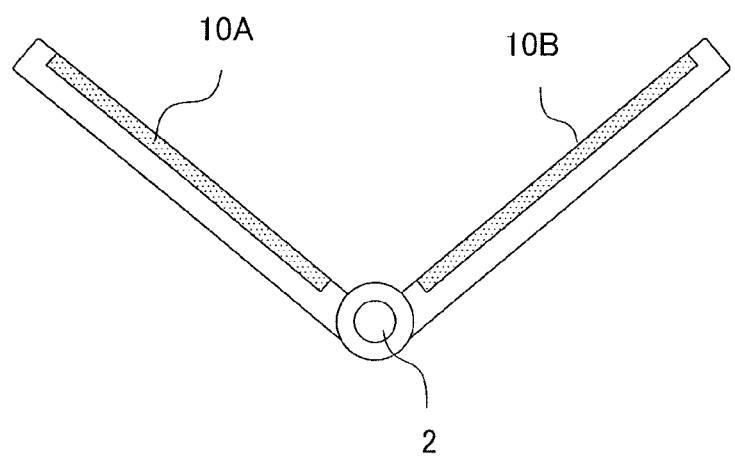

A specific example of such a mirror body will be described. FIGS. 8A and 8B illustrate a mirror body provided with two mirrors, and as shown in the front view of FIG. 8A and the side view of FIG. 8B, it is configured that a pair of mirrors 10A and 10B are coupled in the shape of a hinge, and that the shape-memory portion 2 is connected to the shaft of the hinge. Then, by adjusting the aperture angle of the mirrors 10A and 10B corresponding to the observation site, while bending the shape-memory portion 2 so that the mirrors are in positions preferable to face the observation site, it is possible to obtain various usage methods such as observation from two points by the mirrors 10A and 10B, and the like, and it is possible to secure excellent visibility.

Figure 9A:
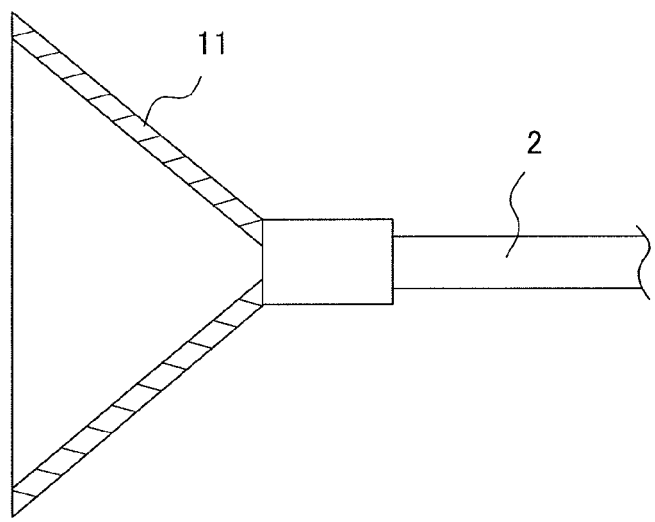
FIGS. 9A and 9B contain explanatory views showing another example of the mirror when the functional portion is the medical mirror in the medical instrument according to the Embodiment of the invention.
Figure 9B:
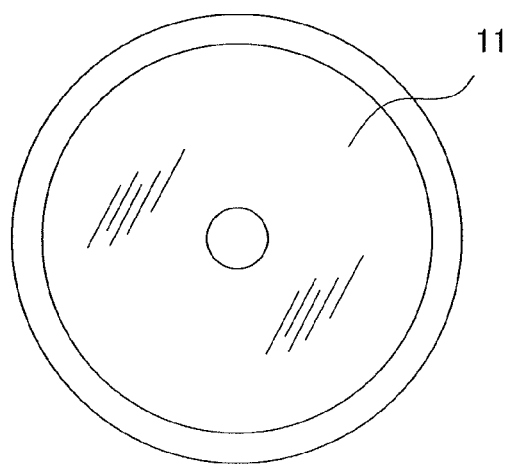
Figure 12:
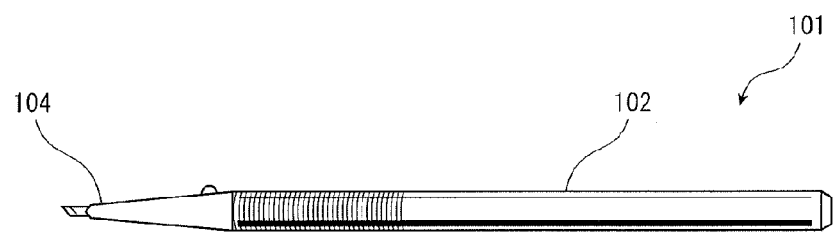
FIG. 12 is a schematic view (Part 1) showing an example of conventional medical knives.
Figure 13:
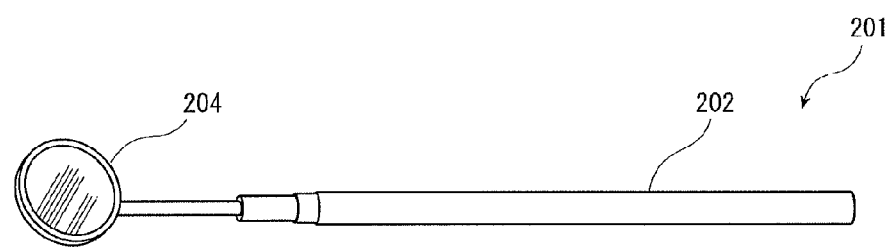
FIG. 13 is a schematic view showing an example of conventional medical mirrors.
Figure 14:
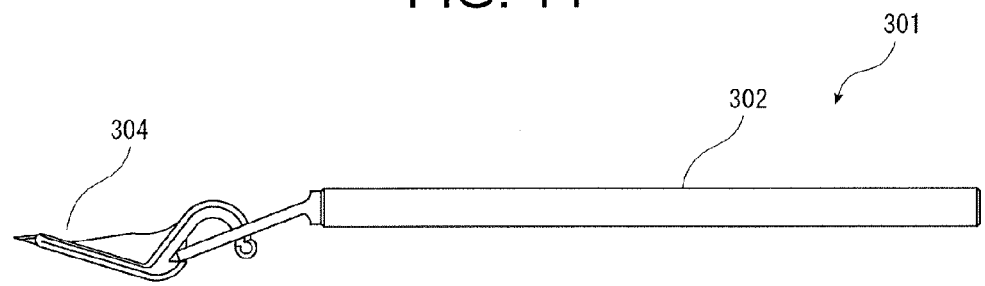
FIG. 14 is a schematic view (Part 2) showing another example of conventional medical knives.

FIGS. 9A and 9B illustrate a mirror body formed in the shape of a cone. As shown in the cross-sectional view of FIG. 9A and the front view of FIG. 9B, the mirror body is connected to the shape-memory portion 2 in the vertex of the cone, while the inner surface of the cone is a mirror surface, and it is configured to enable the observation site to be observed from the 360-degree direction.

Described next is the case of using the medical instrument according to the invention as a medical retractor. As shown in FIG. 10A, a retractor body is used in the functional portion 3, and is connected to the shape-memory portion 2. The medical retractor is an instrument to use in elevating body tissue or securing a space to perform operation work in medical operations, retractor bodies with various dimensions and shapes are prepared as the functional portion 3 corresponding to the purposes, and the retractor body is connected to the shape-memory portion 2. For example, the retractor body as shown in FIG. 10A is configured by bending a flat plate made of metal in the shape of a J as shown in the side view (i) and the front view (ii) in FIG. 10B. Further, the retractor body as shown in FIG. 100 is configured by bending a flat plate made of metal in the shape of an L as shown in the side view (i) and the front view (ii).

In the case of using the medical instrument according to the invention as a dilator, as shown in FIG. 11A, a dilator body is used in the functional portion 3, and is connected to the shape-memory portion 2. The dilator is an instrument used mainly in the case of enlarging the diameter of a blood vessel, and is inserted in the blood vessel through a guide wire once inserted in the blood vessel, and dilator bodies of various shapes are prepared corresponding to diameter sizes in the range of 0.5 mm to about 9.0 mm. FIGS. 11B to 11D show typical shapes of dilator bodies corresponding to diameter sizes.

By configuring as described above, the medical instrument of this Embodiment is provided with the holding portion 1A in which is inserted one end of the shape-memory portion 2, thereby (1) secures the dimension in the longitudinal direction of the shape-memory portion 2 to increase versatility of the position to displace the functional portion 3 by bending, (2) is capable of restricting deformation of the shape-memory portion 2 beyond the predetermined range by the holding portion 1A, and (3) enables the force from the grasp portion 1 or holding portion 1A to be transferred reliably to the functional portion 3 in operating the instrument with the shape-memory portion 2 supported by the holding portion 1A. Then, by further providing the functional portion 3 with the receiving portion 3A, the advantages in above-mentioned (1) and (2) are further enhanced.

In the above-mentioned description, the Embodiment of the present invention is described, but the invention is not limited to the above-mentioned Embodiment, various modifications thereof are capable of being made based on the subject matter of the invention, and the modifications are not excluded from the scope of the invention.

INDUSTRIAL APPLICABILITY

The present invention relates to medical instruments such as a knife, mirror, hook, retractor and dilator used in the medical field, and more particularly, to medical instruments that enable a functional portion provided at the front end of the instrument to be detachable, while enabling the angle between the functional portion and the grasp portion to be changed freely, and has industrial applicability.

DESCRIPTION OF SYMBOLS

1 Grasp portion
1A Holding portion
1B Inner edge portion
2 Shape-memory portion
3 Functional portion
3A Receiving portion
3B Inner edge portion
$d_1, d_2$ Gap

The invention claimed is:

1. A medical instrument comprising:
a functional portion used in medical practice at a front end of the medical instrument;
a rod-shaped grasp portion at a back end of the medical instrument to grasp to operate the functional portion by a user; and
a connection portion made of a straight rod connecting the grasp portion at the back end of the medical instrument in a longitudinal direction thereof and the functional portion at the front end of the medical instrument in the longitudinal direction thereof,
wherein the grasp portion comprises a pipe portion having a straight shape in a predetermined length in the longitudinal direction and an opening on a side of the front end of the medical instrument, and integrally formed in the grasp portion at a side of the connection portion in the longitudinal direction thereof,
the connection portion is made of a shape-memory alloy which is memory-treated in a straight-shape, deformable in a bending direction with a predetermined force, and formed such that an operation of the grasp portion by the user is transferred to the functional portion without deforming in the bending direction when in use,
the connection portion is integrally connected with the grasp portion by connecting an end part of the connection portion at the side of the back end of the medical instrument inserted from the opening at the side of the front end of the medical instrument with an inside of the pipe portion,
the connection portion connected to the grasp portion has a gap provided between an inner surface of the pipe portion and an outer surface of the connection portion in an entire circumference thereof at a part of the connection portion at the side of the back end of the medical instrument inserted into the pipe portion when the connection portion is in a straight condition,
the gap is formed such that the part of the connection portion at the side of the back end of the medical instrument is deformable in the bending direction of the pipe portion freely until the outer surface of the connection portion contacts an inner circumferential edge of the pipe portion and the connection portion is returnable to an original straight shape by heating the connection portion to a memory recovery temperature, and
surfaces of the grasp portion and the functional portion are provided with knurling processing and/or satin finish in order for fingers not to slip when an operator grasps to operate.

2. The medical instrument according to claim 1, wherein the opening of the pipe portion is flared outwardly toward the functional portion.

3. The medical instrument according to claim 1, wherein the connection portion is made of a nickel-titanium alloy.

4. The medical instrument according to claim 1, wherein the functional portion is any one of a medical knife, a medical mirror, a medical hook, a medical retractor and a dilator.

5. The medical instrument according to claim 1, wherein the functional portion is a medical mirror, and
the medical mirror is configured by coupling a pair of mirrors in a shape of a hinge, and the connection portion is connected to a shaft of the hinge.

6. The medical instrument according to claim 1, wherein the functional portion is a medical mirror, and
the medical mirror is formed in a shape of a cone with a connection with the connection portion being a vertex, and an inner surface of the cone is a mirror surface.

7. The medical instrument according to claim 1, wherein an end of the pipe portion is flared toward the functional portion and another end of the pipe portion is connected to the grasp portion.

8. The medical instrument according to claim 1, wherein the connection portion and the functional portion are connected by a screw.

* * * * *